United States Patent
Soto-Eguibar et al.

(10) Patent No.: US 8,855,774 B2
(45) Date of Patent: Oct. 7, 2014

(54) VESTIBULAR PROSTHESIS

(75) Inventors: Enrique Soto-Eguibar, Puebla (MX);
Maria Del Rosario Guadalupe Vega-Y Saenz De Miera, Puebla (MX); Tamara Alexandrova, Puebla (MX); Vladimir Aleksandrov, Puebla (MX); Maribel Reyes Romero, Puebla (MX); Adriana Cristina Pliego Carrillo, Puebla (MX); Wuiyevaldo Fermin Guerrero Sanchez, Puebla (MX)

(73) Assignee: Benemerita Universidad Autonoma de Puebla, Puebla (MX)

( * ) Notice: Subject to any disclaimer, the term of this patent is extended or adjusted under 35 U.S.C. 154(b) by 0 days.

(21) Appl. No.: 13/619,105

(22) Filed: Sep. 14, 2012

(65) Prior Publication Data
US 2014/0081346 A1 Mar. 20, 2014

(51) Int. Cl.
*A61N 1/372* (2006.01)
(52) U.S. Cl.
USPC .................................. 607/45; 607/137
(58) Field of Classification Search
USPC .................................. 607/45, 137
See application file for complete search history.

(56) References Cited

U.S. PATENT DOCUMENTS

2005/0267549 A1 12/2005 Della Santina et al.
2012/0022616 A1* 1/2012 Garnham et al. ............... 607/60

FOREIGN PATENT DOCUMENTS

WO WO 2011/088130 A2 7/2011
WO WO 2012/018631 A2 2/2012

\* cited by examiner

*Primary Examiner* — Joseph Dietrich
(74) *Attorney, Agent, or Firm* — Arent Fox LLP

(57) ABSTRACT

A vestibular prosthesis includes micro-electric-mechanical (MEMS) sensors, gyroscopes in each sensitivity axis (X, Y, Z), accelerometers in each sensitivity axis (X, Y, Z) to detect an angular and linear movement providing displacement measurements, gyroscopes in each one of the spatial axes (X, Y, Z), a microprocessor connected to the MEMS sensors and producing an electric pulse pattern or a continuous galvanic current pattern, a conditioning unit that amplifies and conditions the microprocessor output to apply current to the stimulation electrodes, the microcontroller being configured to determine the displacement of the cupula and the otolithic mass, determine a membrane potential as a result of a displacement detected by the MEMS sensors by means of determining a transduction current, and determine an action potential discharge pattern for the primary afferent neuron, which synapses with the hair cell by means of a mathematical model of the informative process of the vestibular mechanoreceptor.

6 Claims, 9 Drawing Sheets

VESTIBULAR PROSTHESIS

BACKGROUND OF THE INVENTION

1. Technical Field of the Invention

Aspects of the present invention relate to prosthesis for people that suffer from peripheral vestibular disorders. In particular, aspects of the invention relate to a vestibular prosthesis that uses a neuromimetic model of the vestibular function.

2. General Background of the Invention

The peripheral vestibular apparatus resides in the inner ear and is located in the interior of the temporal bone in the bony labyrinth at the base of the cranium. This apparatus is responsible for the transduction of movement during changes in the dynamics of the primary vestibular neurons; the central vestibular nuclei comprise a group of neurons from the brainstem that are responsible of receiving, integrating and distributing the information controlling a set of motor activities, such as the movement of the eyes and the head; postural reflexes, autonomic reflexes and the generation of a spatial framework of the subject's movement within his or her environment, resulting in an efficient posture control, gaze stabilization and the generation of a spatial navigation map for the subject.

FIG. 1 schematizes the human vestibular system, which is constituted by a peripheral part (sensory receptors and afferent and efferent nerve pathways) and a central part (vestibular nuclei and their secondary connections with the brain cortex and other cephalic regions). The Utricle (U), Saccule (S) and the Superior (AC), Lateral (LC) and Posterior (PC) Semicircular Canals can be identified in the peripheral part. At a central level, the vestibular nerves project to the lateral (LVN), descending (DV), medial (MVN) and superior (SVN) vestibular nuclei. The vestibular sensory receptors are constituted by three semicircular canals located in three planes (horizontal and two anterior-posterior vertical planes) and by two otolithic membranes: the utricle and the saccule. The semicircular canals are formed by a hemicanal and a widened section known as the ampulla (anterior ampulla, horizontal ampulla and posterior ampulla) that has a region of sensitive cells itself (hair cells) and in which the sensitive portion presents two elements: one element formed by a gelatinous mass called cupula and another element with epithelium called ampullary crest, presenting supporting and hair cells.

The otolithic organs (saccule and utricle) are formed by an epithelial sac in which the sensory cells accumulate in a region of the epithelium (macula) with supporting cells and hair cells. There is a gelatinous mass on the epithelium known as otolithic mass, formed by calcium carbonate crystals (otoconia), embedded in a gelatinous matrix and surrounded by the otolithic membrane.

Mechanical stimuli have a different influence on each vestibular sensor: angular acceleration produces an inertial movement of the endolymph, flexing the cupula of the semicircular canals, and with them, the cilia of the sensory cells. Linear acceleration produces a displacement of the otolithic mass, which flexes the cilia bundle of the sensory cells of the macula's epithelium. Finally, in both types of organs, the result is the same: the cilia of the sensory cells are flexed. The displacement of the cilia bundle increases the aperture probability of the transduction channels, thus modifying the transduction currents. FIG. 2 shows the cellular process from acceleration until the activation of the vestibular afferent nerve. These are the processes whose sequence constitutes the basis of the mathematical model for the processing of information given by the gyroscope and the accelerometer.

The transduction current causes the hair cells to vary the membrane potential, followed by changes in the membrane's ionic currents, synaptic activation and the subsequent modification of the probability of generating action potentials in the afferent neurons.

The information transmitted from the vestibular organs informs the nervous system about the changes in the direction of the angular (turns) and linear movement. Having this information at its disposal, the brain is capable of correcting any imbalance related to the vestibular processes by means of the modification of the skeletal musculature's contraction. The vestibular system helps to correct posture, in addition to intervening in the displacement of the eyes. It should be noted that, in terms of balance, the vestibular system is the most specific receptor of the balance function from the triad of sensory receptors (proprioceptive, visual and vestibular) because, even though the three contribute to that function, the other two sensory systems, the proprioceptive and the visual, have other functions. The role of the vestibular system can be summarized in three necessary functions to preserve balance:

A. Formation of the sensation of spatial orientation

B. Preservation of body balance; reflexes at rest and in movement.

C. Stabilization of the head and the position of the eyes.

The main function of the vestibular system is to provide information about the spatial orientation of the head. Due to the fact that the vestibular apparatus provides this information regarding the head, it cannot make posture adjustments on its own. The sensors on the neck and maybe on other postural muscles are important to indicate related changes between the head and body to the central nervous system. This information is integrated at a central level, where, added to the proprioceptive and visual information, it allows establishing schemes for the position and dynamics of the organism's displacements. This complex process depends, therefore, on the visual environment and the control of the position of the eyes on the one hand, and on the other, on the information derived from the somatosensory and vestibular systems.

The diminished balance capacity, often considered in senior adults, poses a serious health hazard due to a greater probability of falling down. Vestibular alterations cause blurry or double vision, balance difficulties and the spatial symptoms of disorientation, vertigo, postural imbalance, nausea, vomit, among others, which are often signs of a vestibular system dysfunction. Symptoms can be mild or very severe and long lasting, resulting in total disability with a subsequent high economic cost. Several proposals to improve the sensation of balance and postural control can be taken into account. The appropriate medication can reduce some of the symptoms. Non-invasive exercises have a relatively low risk and can also improve vestibular function. If balance control cannot be improved using these methods, a vestibular prosthesis is an alternative way of restoring the balance function. Said device can be applied as a temporary aid during the recovery of an inner ear surgery or as a permanent prosthesis for subjects with severe vestibular damage and in senior adults prone to falling down.

In fact, for the person in the process of falling, it is more important to be able to "land" safely than to prevent a future fall. In cats, monkeys and human beings, the "landing" response depends, at least in part, on the vestibular function. In an extreme situation, the fall takes place during a very short period of time, not exceeding one second. Therefore, a 10-20-millisecond delay in the output signal of the vestibular apparatus (because of deterioration due to old age or because of a vestibule-specific pathology) leads to an unavoidable (uncontrollable) fall. The second cause of the uncontrollable fall is the quantitative change in the output signal, such as the loss of information of the otolithic organ or the semicircular canal, for example.

Due to the high incidence of vestibular alterations and their disabling effects, some vestibular prosthesis and aids have been developed. These consist of at least two categories. In a first category, the vestibular prosthesis provides information to the nervous system directly through the electrical stimulation of the vestibular pathways related to spatial orientation. In a second category, the vestibular prosthesis provides information via sensory substitution through the other sensory systems (tactile, visual, auditory, etc.).

Regarding the devices of the first category, research is currently being carried out to develop fully implantable vestibular prostheses, designed with Micro-Electric-Mechanical-System (MEMS) technology, consisting of gyroscopes and accelerometers, as well as integrated circuits (CI). The operation of these devices is based on the capacity to detect the acceleration the head is subjected to and the possibility of injecting pulses to the vestibular part of the brain. The following sensitivity parameters, among others, are taken into account: (a) the rotational perception threshold and (b) the linear acceleration sensitivity threshold in human beings, as well as (c) the neuron discharge rate and its relationship with the head's movements and rotations.

The vestibular prostheses in the second category are non-invasive in nature, that is to say, they do not need implants and are based on methods that allow the subject to obtain information about the acceleration the head is subjected to by means of other sensory organs (a sound or an electric stimulus on the skin, for example). In this case, the subject's adaptive plastic capacity and learning capabilities play an essential role in the operation of the prosthetic system.

Vestibular prostheses to aid the treatment of balance disorders in human beings are currently being researched. For example, Rubinstein and Phillips of the University of Washington's Medical Centre announced in October 2011 that one patient would be the first receptor in the world of an implant whose objective is the treatment of vertigo related to Meniere's disease (Meniere's disease is an inner ear disorder affecting the person's balance and hearing. The balance problems associated to this disease are produced due to an alteration in the inner ear's fluids with an endolymph accumulation). Up to now, this disease had been treated with medication, diet changes, exercise, and in the most severe cases, surgery. However, surgery normally means having to give up the capacity to hear in the affected ear with the purpose of stopping vertigo. The device developed by Rubinstein and Phillips of the University of Washington's Medical Centre, which is still being tested, is based in the commercial technology for cochlear implants with an electrode arrangement and a processor with software designed for its specialized use.

The patient carries a processor behind the auricle of the affected ear and, when an attack begins, the patient activates the device so that it operates during the periods when the vertigo takes place only. Said device transmits electrical impulses through three electrodes inserted in the canals of the bony labyrinth of the inner ear. The intensity of the stimulus and the efficiency of the vertigo suppression must be modulated with amplitude and frequency adjustments. Each semicircular canal receives an electrode arrangement.

Another device being researched is the one developed by Andrei Shkeel and collaborators from Irvine University in California. They are working in the design of a unilateral vestibular prosthesis whose detection element is a MEMS one-axis gyroscope. Similar to the semicircular canals, the microgyroscope detects the head's angular movements and generates proportional voltages to those corresponding to angular acceleration. The output of these detectors is sent to a pulse-generating unit, where the angular movement is translated into voltage pulses. The monophasic voltage pulses become biphasic current pulses and are conditioned to stimulate the corresponding branch of the vestibular nerve. On the other hand, Gong and Merfeld from Harvard University's Harvard Clinical and Translational Science Centre are researching a neural prosthesis of the semicircular canal using electrical stimulation. The device measures the head's angular velocity with a microgyroscope. The velocity is filtered digitally to modulate the frequency of the electrical stimulation pulse. The pulse varies between 50 and 250 Hz through a value table relating angular velocity to pulse frequency in a sigmoidal manner. A power source uses these pulses to deliver a balanced charge in the form of current pulses to the nerves innervating the semicircular canals through platinum electrodes. All the components of the device are found inside a light container measuring 43 mm×331 mm×325 mm approximately, which can be assembled in the upper part of the head.

Another device is the one developed by Charley C. Della Santina and collaborators from John Hopkins University in the United States, international patent applications WO-2011/088130, WO-2012/018631, United States patent application US-2005-0267549, in which the operation of a vestibular prosthesis that codifies three-dimensional movement to electrical impulse stimuli with a modulated frequency, with which the ampullary nerves are stimulated, is to described. This device has been studied in experimental animals, in which the ampullary nerves are stimulated, thus provoking turning responses and compensatory responses accompanied by—vestibule-ocular reflexes.

The international patent application WO 2011/088130 A2 (SANTINA, COLEMAN, FRIDMAN and CHIANG), published on Jul. 31, 2011, describes; an implantable vestibular prosthesis in which the device has a sensor system, a data processor connected to the sensor system and a nerve stimulation system connected to the data processor in order to provide electrical stimulation to at least one branch of at least one vestibulocochlear nerve. The nerve stimulation system includes an electrode arrangement with a first group of electrodes structured to be surgically implanted through an electrical connection with an upper pathway or branch of the vestibular nerve; a second group of electrodes structured to be surgically implanted through an electrical connection with a horizontal pathway or branch of the vestibular nerve; a third group of electrodes structured to be surgically implanted through an electrical connection with a posterior pathway or branch of the vestibular nerve; and a common cross electrode structured to be surgically implanted within the common cross of the vestibular labyrinth.

WO 2012/018631 A2 (SANTINA, COLEMAN, ANDREOU, KALAYJIAN, FRIDMAN and CHIANG), published on Feb. 9, 2012, describes a multi-channel vestibular prosthesis comprising: a sensor system; a microcontroller configured to communicate with the sensor system to receive the signals registered by the sensors while in operation, said microcontroller being configured to provide control signals in response to the signals from the sensors (registered); an integrated neuro-electronic interface circuit configured to communicate with the microcontroller to receive said control signals; and one group or set of electrodes electrically connected to said integrated neuro-electronic interface circuit; in which said integrated neuro-electronic interface circuit comprises: a digital controller configured to communicate with the microcontroller; a set of digital-to-analogue to converters configured to communicate with the digital controller; and a set of analogue current control circuits, each one of which is built to communicate respectively with each other; in which each one of said group of analogue current control circuits can be connected electrically to a respective electrode from a group of electrodes to deliver an electrical stimulus to at least one vestibular nerve, either directly or under software control; and in which said digital controller is configured to control amplitude, frequencies, polarities and duration of the currents to be delivered to any combination of said group of electric conductors.

These developments are incipient, however. The state of the art does not include a vestibular prosthesis that reproduces the processing of the natural vestibular information to mechanical stimuli (because the matter object of aspects of the present invention is a vestibular prosthesis). Therefore, there is a need for a vestibular prosthesis that compensates the loss of a person's vestibular function and related functions in the state of the art.

SUMMARY OF THE INVENTION

An example object of aspects of the present invention is to provide a neuromimetic vestibular prosthesis for the stabilization of the vertical posture during a normal situation and in extreme situations, such as, for example, in the case of a trip or a shove.

Another example object of the invention is to provide a vestibular prosthesis that is able to send electrical stimuli, whose characteristics depend on the intensity of the mechanical stimulus due to the acceleration of the head, thus preventing a fall.

Another example object of the invention consists in providing a vestibular prosthesis to make calculations in a very short time such as, for example, less than 10-20 milliseconds, and transform them into electrical signals in order to stimulate the vestibular nerves on time so that this device can help prevent a fall.

Another example object of the invention is providing an electrode system for to electrical stimulation in the periauricular region, which would allow the subject to stabilize his or her posture without having to implant a microelectrode system. According to various aspects, the electrode may be a diadem-shaped electrode.

The previous example objects may be achieved by means of providing a vestibular prosthesis, having:
micro-electric-mechanical (MEMS) sensors; at least one pair of gyroscopes in each sensitivity axis (X, Y, Z), at least one pair of accelerometers in each sensitivity axis (X, Y, Z) or at least two accelerometers with three sensitivity axes to detect an angular and linear movement providing displacement measurements; two gyroscopes in each one of the spatial axes (X, Y, Z); a microprocessor, connected to the MEMS sensors and producing an electric pulse pattern—mode 1—or a continuous galvanic current pattern—mode 2—; a conditioning unit that amplifies and conditions the microprocessor output to apply the current, proportional to said output, to the stimulation electrodes; where the microcontroller is configured to: determine the displacement of the cupula and the otolithic mass; determine a membrane potential $V_1$ as a result of a displacement x detected by the MEMS sensors by means of determining a transduction current $I_T$; and to determine an action potential discharge pattern $V_2$ for the primary afferent neuron, which synapses with the hair cell by means of a mathematical model of the informative process of the vestibular mechanoreceptor.

BRIEF DESCRIPTION OF THE DRAWINGS

Aspects of the present invention will be completely understood by means of the detailed description given below and the attached drawings, which are provided by way of illustration and example only and therefore, do not limit the aspects of the present invention, in which.

DETAILED DESCRIPTION OF THE INVENTION

Figure 1:
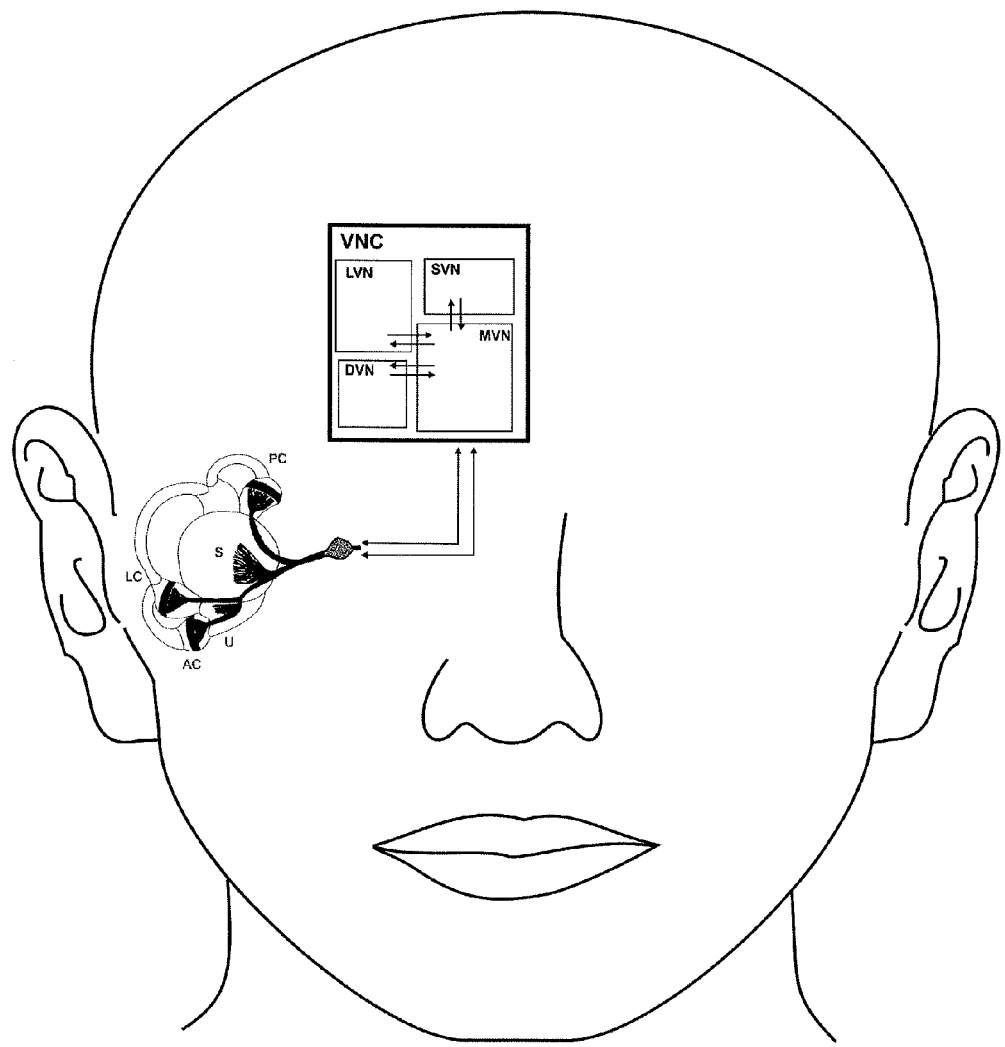
FIG. 1. Shows a general scheme of the vestibular system in its peripheral part and its projections towards the vestibular nuclei in the brainstem.

The various example aspects of the present invention are described in more detail below, referring to the drawings (figures, schemes and graphs) attached, in which the variations and the aspects of the present invention are shown. The various example aspects of the present invention may, however, be carried out in many different ways and should not be interpreted as limitations to the variations established in aspects of the present invention; on the contrary, the variations are provided so that this description is complete in the illustrative implementations and the scope of the same is fully transmitted to the experts in the technique.

Unless otherwise defined, all the technical and scientific terms used in this document have the same meaning as normally understood by an expert in the art to which the aspects of the present invention belong. The apparatuses, systems and examples provided in this document are illustrative only and do not intend to be limiting.

To the extent that the mathematical models are able to reproduce the magnitudes reported in the experiments, they can still be considered to model diverse natural processes. Therefore, a model for the vestibular function incorporated to a vestibular prosthesis in considered in this invention.

Various aspects of the present invention describe a simulation of the informative process of the vestibular function by means of a data microprocessor configured to develop/reproduce a mathematical model and its application as a vestibular function simulator in the stabilization process of the vertical posture, and the manner in which to use this model for its application in a vestibular prosthesis is described.

Various aspects of the present invention include a vestibular prosthesis that is helpful for people who suffer peripheral vestibular disorders and that may suffer incontrollable falls. The vestibular prosthesis of aspects of the present invention is a device that transforms a mechanical stimulus (the head's acceleration) into a group of electric signals with which the vestibular pathways are stimulated, whether directly (mode 1—invasive implantation) or through superficial electrodes (mode 2—galvanic stimulation).

The device of aspects of the present invention uses a high-level processing based on a neuromimetic model of the vestibular function. This model has been developed by imitating the functions of the natural organ and consists of a mathematical system of differential equations, which is in charge of converting the micro-electric-mechanical (MEMS) sensor output into electrical impulse patterns (mode 1, pulse-based stimulation) or DC voltage variation patterns (mode 2, galvanic current-based stimulation) in the form (amplitude, frequency and temporal modulation) of the vestibular organ's natural response to similar stimuli and that stimulates the vestibular system by imitating the natural function of said system.

According to aspects of the present invention, the MEMS sensors may be used as electromechanical analogue sensors of the natural vestibular sensors, and may include microgyroscopes that detect angular movements in order to carry out an identical function than the one carried out by the semicircular canals, and micro-accelerometers that detect static linear acceleration due to the gravitational pull, and the apparent linear acceleration in an analogous fashion as the otolithic organs, that is to say, the saccule and the utricle.

According to an example embodiment of the invention, the MEMS sensors can be placed behind the auricle or in the upper part of the head, whether bilaterally or unilaterally, in order to detect the acceleration the head is subjected to (at rest or in movement, during this process the person might be subject to falling situations, such as, for example, a trip or a shove). The information (acceleration data) obtained from these sensors constitutes an input (mechanical stimulus) for the vestibular function model.

Figure 3:
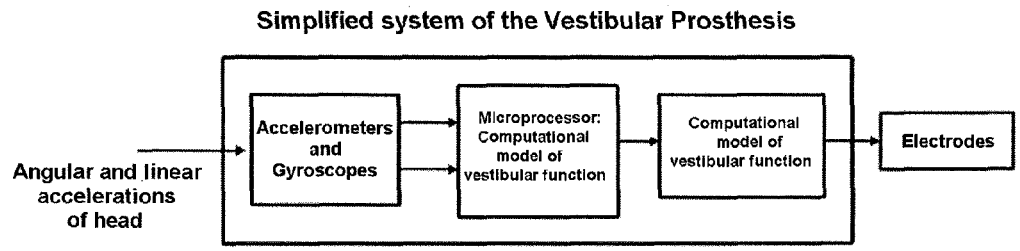
FIG. 3. Shows a simplified scheme of the vestibular prosthesis according to various aspects of the present invention.

The vestibular prosthesis of aspects of the present invention includes a microprocessor that uses the mathematical model of the vestibular function (see FIG. 3), which reproduces the informative process at the semicircular canals and the saccule from the movement in which they detect a mechanical stimulus (the head's accelerated movement) until the generation of action potentials per each afferent neuron in each vestibular sensor. This model simulates the natural vestibular function in the stabilization process of the vertical posture before a mechanical stimulus that could cause a fall, thus obtaining the action potential generation frequency constituting the electric signal integrated to the brain to generate the postural reflexes contributing to the preservation of the vertical posture by means of said stimulus.

Mathematical Model of the Vestibular Function and its Technical Implementation

The mathematical model of the vestibular function describes the informative process from the very moment when the vestibular organ detects a mechanical stimulus until the activation of the vestibular afferent nerves that take the information related to said mechanical stimulus to the brain.

Unlike other inventions, the model of aspects of the present invention is a neuromimetic model. That is to say, its design is based on the physiological processes that take place in the vestibular system naturally. In fact, the model is based on the results of basic research carried out and published, in its majority, by researchers from BUAP's Physiology Institute.

The present model is characterized in that it is a model formed by several steps, whose activity is determined by the functional interaction of five different steps, which are illustrated below:

TABLE 1

General scheme of the mathematical model of the vestibular function.

(1) $\frac{d^2x}{dx^2} + \frac{1}{\tau_1}\frac{dx}{dt} + \frac{1}{\tau_1\tau_2}x = \frac{R_1}{k_1^2}\left(1 + \frac{l_1}{L_1}\right)\frac{d\omega}{dt}$ — Mechanical coupling at a vertical semicircular canal (2) $M + \frac{d^2X}{dX^2} + K_e\frac{dX}{dt} + K_cX = M - (G - W)_x$ — Mechanical coupling at the saccule (2) $I_{Tr} = g_{Tr}(x, s)(V_1 - E_{Tr});$
$g_{Tr} = g_{Tr}p(x, s); p(x, s) = \frac{1}{1 + e^{\frac{x+s-x_0}{s_1}}}$ — Mechanoelectrical transduction (3) $C_{m1}\frac{dV_1}{dt} = -I_{Tr} - I_T - I_{L1}$
$I_T = g_T m^3(h_1 + h_2)(V_1 - E_T)$
$I_L = g_L V_1$
$\tau_m(V_1)\frac{dm}{dt} = (m_{ST}(V_1) - m)Q_{10}$
$\tau_{h1}(V_1)\frac{dh_1}{dt} = (q_1 h_{ST}(V_1) - h_1)Q_{10}$
$\tau_{h2}(V_1)\frac{dh_2}{dt} = (q_2 h_{ST}(V_1) - h_2)Q_{10}$ — Dynamics of the hair cell's membrane potential (4) $I_{Syn} = \phi(V_1)$ — Synaptic Transmission (5) $C_{m2}\frac{dV_2}{dt} = I_{Syn} - I_{Na} - I_K - I_{L2}$
$I_{Na} = g_{Na}^{max}(m_\infty(V_2))^3(C(V_2) - n)(V_2 - V_{Na})$
$I_K = g_K^{max} n^4 h_K(V_2 - V_K)$
$I_{L2} = g_{L2}^{max}(V_2 - V_L)$
$\tau_n(V_2)\frac{dn}{dt} = (n_\infty(V_2) - n)Q_{10}$
$\tau_h(V_2)\frac{dh}{dt} = (h_\infty(V_2) - h)Q_{10}$ — Dynamics of the primary afferent nerve cell's membrane potential In which:

Step 1. Relates to the dynamics of the mechanical coupling of the cupula-endolymphatic system and the model of the otolithic mass that simulate the vestibular function in the semicircular canals and the otolithic organs respectively;

Step 2. Relates to the mechanoelectrical transduction mechanism in the hair cell;

Step 3. Relates to the dynamics of the membrane potential in the hair cell;

Step 4. Relates to synaptic transmission; and

Step 5. Relates to the dynamics of the membrane potential of the primary afferent nerve cell, the activation of the bipolar afferent neuron and the generation of action potentials.

Figure 2:
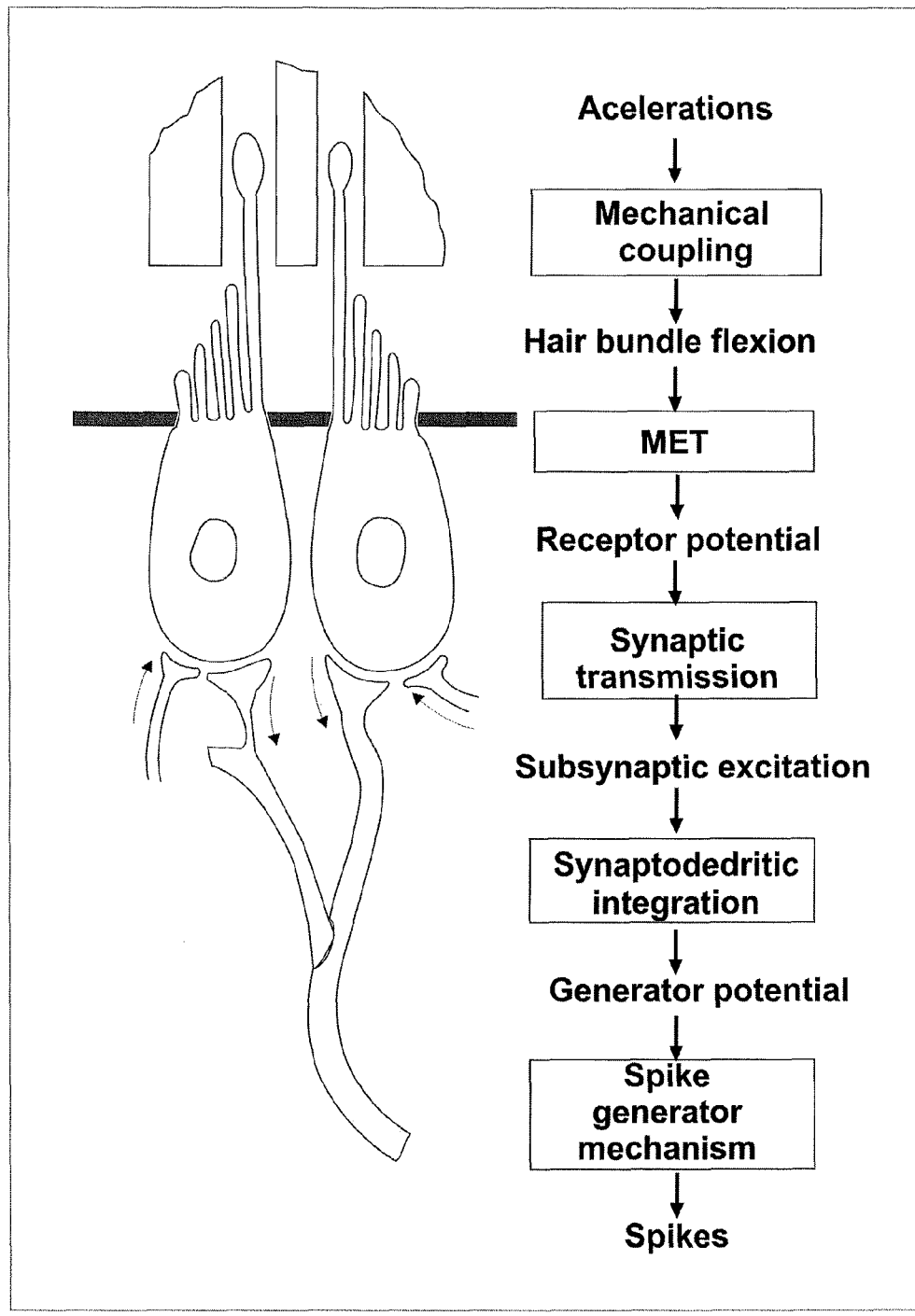
FIG. 2. Shows a scheme of the cellular processes ranging from the appearance of an acceleration to the activation of the vestibular afferent nerve.
Figure 4:
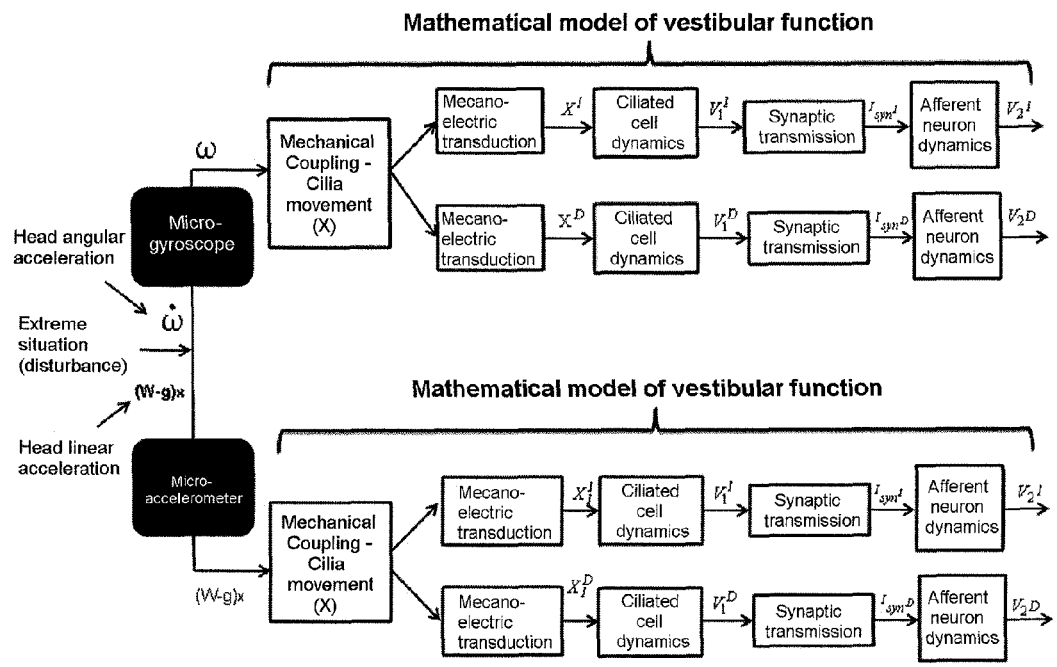
FIG. 4. Shows a block scheme of the vestibular prosthesis, according to various aspects of the present invention.

These steps and their anatomical equivalent in the vestibular system are illustrated in FIGS. 2 and 4.

The vestibular mechanoreceptor model's input is the mechanical coupling of is the cupula-endolymphatic system and the otolithic mass model (step 1), which stimulate the vestibular function at the semicircular canals and at the saccule, respectively.

In order to develop the neuromimetic model, a set of differential equations describing the behaviour of the system in mathematical and physical terms in detail has been elaborated. Subsequently, a set of mathematical simplifications has been developed so that real instead of theoretical solutions are obtained for the natural input to the vestibule, represented by the linear and angular acceleration the head is subjected to. The present model is helpful from a technical point of view because it can be quickly solved—online—by a standard RISC (reduced instruction set) merchant microprocessor.

This technical solution of a highly sophisticated neuromimetic model in real time is a contribution of aspects of this invention because it allows processing stimuli in the form of the angular and linear acceleration detected by the accelerometers and the gyroscopes "in real time" and generating an output in the form of electrical impulse patterns (mode 1, pulse-based stimulation) or DC voltage variation patterns (mode 2, galvanic current-based stimulation) in the form (frequency and temporal modulation) of the vestibular organ's natural response to similar stimuli.

In the subjects to which the prosthesis is applied, the activity patterns of the vestibular prosthesis generated in this manner will produce an activity of the vestibular nerve similar to that naturally produced by such stimuli, effectively reproducing the response of the vestibular organ.

This example model is able to describe/reproduce the informative process at the peripheral vestibular system during the vertical posture stabilization process to in extreme situations (that could cause a fall) in the sagittal plane. See FIG. 4 and Table 1.

The output information of this model is a set of electrical impulses ($V_2$) with different frequencies, amplitudes and variable polarities, or the modulation of the galvanic current's amplitude, polarity and frequency, which depend on the intensity of the stimulus. In the natural organs, the frequencies with which the signals are sent through the vestibular pathways towards the brain determine posture control. The frequency of the appearance of these pulses is calculated with the help of the vestibular function model for a given stimulus, thus obtaining the information required by the brain to detect the angular and linear acceleration the head is subjected to and to generate the necessary reflexes to control posture. FIGS. 1, 2 and 4 and Table 1 show a general scheme of the vestibule and the equations used for the development of the mathematical model of each one of the steps.

Description of the Steps of the Model and its Equations

Step 1. Relates to the dynamics of the mechanical coupling of the cupula-endolymphatic system and the otolithic mass model that simulate the vestibular function of the semicircular canals and the otolithic organs respectively, where: The sensory cells of the semicircular canals and the otolithic organs are similar. Therefore, the steps 2 to 5 of the mathematical model are similar for the otolithic organs and the semicircular canals. However, these two organs differ in terms of the mechanical coupling process, which is why they have been mathematically modelled on a separate basis. This is also reflected in the fact that the technical equivalents of the otolithic organs are the accelerometers and the technical equivalents of the semicircular canals are the gyroscopes.

In aspects of the present invention, a set of gyroscopes (at least three: one in each spatial plane—X, Y, Z—) carries out the function of the semicircular canals, and a set of accelerometers (at least three: one in each spatial plane—X, Y, Z—) carry out the function of the otolithic organs (utricle and saccule).

Precisely because the gyroscope performs the function of the semicircular canals and the accelerometers perform the function of the otolithic organs in aspects of the invention, these behaviours of the model are simplified in the prosthetic system and the gyroscope and the accelerometer's output are linked to the movement of the cilia, thus simplifying the mechanical coupling equations, which contributes to an effective operation of the model. The canal equations of step 1 (Table 1) are reduced to the following:

$$\ddot{X} + \frac{1}{\tau_2}\dot{X} + \frac{1}{\tau_1 \tau_2}X = k_0 R \dot{\omega}$$

And the Otolithic Organ Equations are Reduced to:

$$X_s = \frac{m_-}{k_{simpl}}(g_s - w_s)$$

Step 2. Relates to the mechanoelectrical transduction mechanism in the hair cell; where:

The mechanoelectrical transduction mechanism carrying out the mechanical energy conversion into electric energy and generating the transduction current is based on results published by Markin and Hudspeth (1995). This model describes the dependence of the transduction current on the displacement of the cilia bundle. The mathematical model of this mechanism is presented in the following form:

$$I_{Tr} = g_{Tr}(x)(V_1 - E_{Tr});$$

$$g_{Tr} = \bar{g}_{Tr} p(x);$$

$$p(x) = \frac{1}{1 + \mathrm{Exp}\left(-\frac{x - x_0}{s_1}\right)};$$

where $I_{Tr}$ is the transduction current; p(x) is the opening probability of the canal; x is the displacement of the cilia bundle and $g_{Tr}$ is the conductance of the canal.

Step 3. Relates to the dynamics of the membrane potential in the hair cell; where:

The membrane potential model of the hair cell being used is based on the well-known Hodgkin-Huxley equations (1952), with a modification proposed according to aspects of the invention, which consists in the proposal that the dynamics of the hair cell can be described using a total ionic current $I_T$, where $I_T$ is the sum of the main ionic currents that are present in the hair cells, in which several types of the $K^+$ current ($I_K$) are unified, including the $K^+$ current activated by $Ca^{2+}$ ($I_{KCa}$).

$$C_{m1}\frac{dV_1}{dt} = -I_{Tr} - I_T - I_{L1}; \quad (2.10)$$

$$I_T = g_T m^3 (h_1 + h_2)(V_1 - E_T); \quad (2.11)$$

$$I_{L1} = g_{L_1} V_1,$$

$$\tau_m(V_1)\frac{dm}{dt} = m_{ST}(V_1) - m \quad (2.12)$$

$$\tau_{h_1}(V_1)\frac{dh_1}{dt} = q_1 h_{ST}(V_1) - h_1 \quad (2.13)$$

$$\tau_{h_2}(V_1)\frac{dh_2}{dt} = q_2 h_{ST}(V_1) - h_2 \quad (2.14)$$

where $V_1$ is the membrane potential, $C_{m1}$ is the membrane capacitance, $I_T$ the total ionic current flowing through the ionic channels, $g_T$ the maximum conductance, $m^r$ the parameter specifying the activation process, h is a parameter specifying the inactivation process, $E_T$ is the balance potential of the total current, $I_L$ is the leakage current and, under natural conditions, $I_{Tr}$ is the current of the transduction channels located in the stereocilia ($I_{Tr}=I_{com}$) or, in the voltage-clamp experiments, it is the command current. The inactivation parameter (h) has two components (h=$h_1$+$h_2$) that correspond to the potassium channels with their fast and slow components, respectively. Here, $q_1$ and $q_2$, which vary between 0 and 1, are the relative fast and slow inactivation components, respectively. The voltage dependence of m, $h_1$ and $h_2$ is given by the functions $m_{ST}(V_1)$ and $h_{ST}(V_1)$. These functions are described by first-order Boltzmann functions. Both the activation and inactivation time constants are also functions of the voltage $V_1$. The approximations for $h_1$ and $h_2$ are by straight lines with small slopes using the parameters $k_{h1}$, $k_{h2}$, $b_{h1}$ and $b_{h2}$.

Step 4. Relates to the synaptic transmission; where:

The following block or compartment of the vestibular mechanoreceptor models the membrane potential in the hair cell ($V_1$) for the generation of the synaptic current in the synaptic cleft. The hair cells release a glutamate-type transmitter whose flux is determined by the presynaptic depolarization and requires the presence of $Ca^{2+}$ in the extra-cellular medium, since the channels that actively participate in the release of the neurotransmitter are the $Ca^{2+}$ and $Ca^{2+}$ activated $K^+$ channels. It was experimentally discovered that the synaptic response in the afferent neurons (the postsynaptic current, $I_{Syn}$) depends on the membrane potential of the hair cell. The fusion index of the synaptic vesicles depends on the amplitude of the $Ca^{2+}$ presynaptic current lineally. In addition, the $Ca^{2+}$ presynaptic current and postsynaptic current have a sigmoidal dependence on the membrane potential of the hair cell (Keen and Hudspeth, 2006).

In the Keen and Hudspeth article (2006), the synaptic current ($I_{Syn}$) is normalized. In aspects of the present invention, we rescaled these values to use the resulting curve as a model for synaptic transmission. The synaptic current is rescaled at a maximum current$_{maximum} I_{syn}$=60 µA/cm$^2$, which has been chosen so that, in the absence of the mechanical stimulus (with the help of the vestibular mechanoreceptor model), action potential discharge frequencies for the afferent neuron ranging between 20-50 Hz are obtained.

The rescaled points were approximated with a three-parameter sigmoidal function: the upper limit, the slope and the inflection point.

This way, the synaptic transmission model remains the following:

$$I_{Syn} = \frac{59.6992}{1 + \exp\left(\frac{-(V_1 40.6031)}{4.5979}\right)}$$

where 59.6992 is the maximum value of the synaptic current (upper limit), 14.5979 is the slope and 40.6031 is the inflection point of the sigmoidal curve approximating the rescaled points.

Step 5. Relates to the dynamics of the membrane potential of the primary afferent nerve cell. Activation of the bipolar afferent neuron and the generation of action potential; where:

In order to model the generation of the action potentials $V_2$ of the primary bipolar afferent neuron, the Hodgkin Huxley equations are used once again, but by applying the simplifications that are part of aspects of our invention once again, we obtain a solution which allow solving those equations in a simplified manner. Thus, the model remains as follows:

$$C_{m2}\frac{dV_2}{dt} = -I_{Syn}(V_1) - I_{Na} - I_K - I_{L2},$$

$$I_{Na} = g_{Na}(m_\infty(V_2))^3(C(V_2)-n)(V_2 - V_{Na}),$$

$$I_K = g_K n^4 h_3 (V_2 - V_K),$$

$$I_{L2} = g_{L2}(V_2 - V_L),$$

$$\tau_n(V_2)\frac{dn}{dt} = n_\infty(V_2) - n,$$

$$\tau_{h_3}(V_2)\frac{dh_3}{dt} = h_{3\infty}(V_2) - h_3$$

where V2(t) is the membrane potential, m(t) is the sodium activation variable, n(t) is the potassium activation variable and h(t) is the sodium inactivation variable, h≤1; VNa; VK are the sodium and potassium balance potentials, respectively; VL is the balance potential of the leakage current; gmax Na, gmax K to and gmaxL are the maximum sodium, potassium and leakage conductances, respectively; Ist is the stimulus current, Cm2 is the membrane capacitance.

Results Obtained by Means of the Mathematical Model of the Vestibular Function

Figure 5:
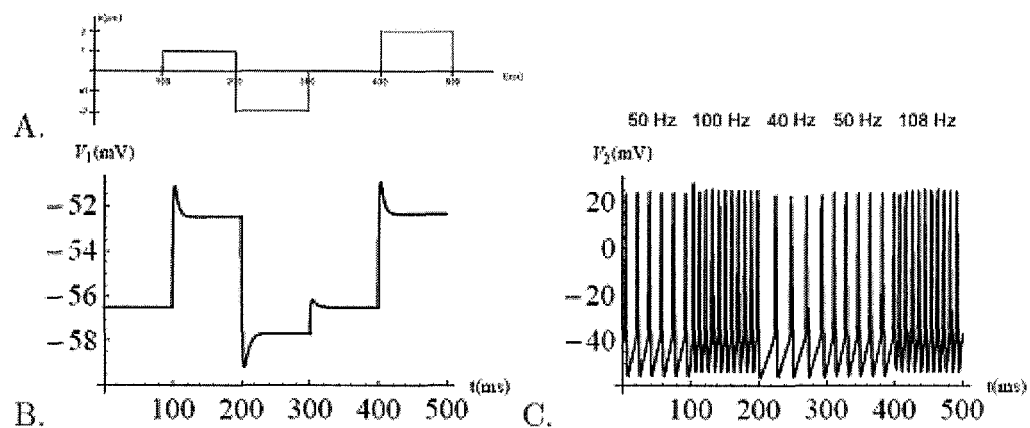
FIG. 5A. Shows the response of the vestibular mechanoreceptor model with the displacement of the cilia bundle of the hair cell graphically, according to various aspects of the present invention.
FIG. 5B. Shows the response of the vestibular mechanoreceptor model with the membrane potential of hair cell V1 graphically, according to various aspects of the present invention.
FIG. 5C. Shows the response of the vestibular mechanoreceptor model with action potential trains V2 graphically, produced at the afferent neuron as a consequence of the mechanical stimulus in the cilia bundle, according to various aspects of the present invention.

The mathematical model of the vestibular function allowed us to demonstrate that the developed set of equations and its simplifications can be used to analyse one input in the form of linear or angular acceleration and to obtain a response similar than the one produced in the natural vestibular system. The graphs shown in FIG. 5 present an application of the model to one input in the form of angular acceleration and the resulting output.

Simulation of the Informative Process in the Saccule

As described in the beginning of the chapter, the main difference between the otolithic organs and the semicircular canals is the mechanical coupling process that, in the case of the saccule and the utricle, is based on the dynamics of the otolithic mass immersed in the endolymph.

Unlike the semicircular canals, the otolithic organs respond to the head's apparent linear acceleration. The apparent linear acceleration is the subtraction of the absolute acceleration and the gravitational acceleration (W−G). For this reason, we named them the gravito-inertial mechanoreceptors. The otolithic mass can be represented as an accelerometer. The saccular or utricular macula (which is the region in which the hair cells are found) obtains information from many sensitivity directions, but the most intense response to a mechanical stimulus causing a fall is observed in the cells located along a sensitivity axis, which is orthogonal to the local vertical at the initial instant of time.

The otolithic organs of the left ear and the right ear provide the same information, so, for the mathematical model, we took into account the information from a single otolithic organ.

In addition, we took into account the information of those cells that are orthogonal to the local vertical at the initial instant of time because they have a greater sensitivity.

Each cell that is found along the same sensitivity direction is the same on the right side and on the left side. Then, for the same stimulus, if the cells with the same sensitivity axis have an exciting response, the cells with their axis in the opposite direction will have an inhibiting response. For this reason, modelling a pair of lines with opposite sensitivity directions to obtain a representation of all the hair cells that are found along the sensitivity axis taken into account will be enough.

In the case of the saccule, the hair cells are flexed due to the inertial movement of the otolithic mass (denser than the fluid surrounding it), which is displaced directly by gravity or by the head's linear acceleration. The otolithic mass' displacement is considered the same than the one the cilia bundle is subjected to.

The displacement of the otolithic mass along a sensitivity axis is described regarding a SXYZ reference system, whose origin is found in the centre of the saccule. During the initial moment, the SY axis is oriented vertically downwards (from the tip of the head to the chin), the SX axis is oriented horizontally from the nose to the back of the head, and the SZ axis is oriented from the right vestibular labyrinth to the left. The movement plane of the saccular otolithic mass is parallel to the SXY plane (and parallel to the saccule's macula).

Since we considered the movement in the sagittal plane and the direction with the greatest sensitivity, then this one corresponds to the SX axis, defined in the previous paragraph.

The displacement relative to the otolithic mass' centre of mass X along the SX sensitivity axis is described by the following equation:

$$M_+ \ddot{X} + k_e \dot{X} + k_c X = M_-(G-W)_x$$

Here, $(G-W)_x$ is the projection over the sensitivity axis X of the apparent acceleration the head is subjected to; $M_+ = V_0 (\rho_0 \beta_{\rho e})$ and $M_- = V_0(\rho_0 - \rho_e)$, where $\rho_0$, $\rho_e$ are the endolymph and the otolithic mass' density, respectively, $V_0$ is the otolithic mass' volume; $ke$ is the endolymph's viscous resistance coefficient; $kc$ is the columnar band's rigidity coefficient. The second and third terms to the left of the equation correspond to the viscous friction force due to the otolithic mass' movement within the endolymph and the elastic force due to the hair cell's columnar band, respectively.

Linear Displacement and Inclination Sensor-Accelerometer

The vestibular prosthesis of aspects of the invention includes a set of at least three accelerometers or three-sensitivity-axis accelerometers whose purpose is to carry out the operation of the utricle and the saccule. Due to the fact that each accelerometer is oriented with a different sensitivity axis in each spatial plane, the scheme of FIG. 4 includes two processing lines schematically.

An accelerometer detects inclination by measuring the effect that the force of gravity exerts on the accelerometer's axes that are exposed to this action depending on their position in space. That is to say, if we consider an accelerometer with three inertial axes (X, Y, and Z), we must consider the three acceleration actions separately to obtain the products (results) of the movement axes.

The majority of the accelerometers that exist in the market nowadays contrast their measurements with the force of gravity and then turn their results into Volts or Bits (in the case of devices with a digital output). This information passes on to a microprocessor/microcontroller and the analysis process of the data acquired takes place there. Unlike the state of the art, the linear acceleration information according to aspects of the present invention is supplied directly to the Mathematical Model of the Vestibular System, which is executed by a microprocessor and its output consists of an electrical stimulation pattern proportional to the neuron discharge calculated based on the model.

Recent technological advances have made it possible to manufacture accelerometers with MEMS technology in the detection ranges for low and high gravity units with much broader bandwidths than before, increasing the field of possible applications in this manner. An accelerometer with a low gravity unit range, with detection values lower than 20 g since the actions of movement that could be generated by a human being are found within this group, was selected for the purpose of aspects of this invention.

The accelerometer, helpful for the vestibular prosthesis of aspects of the present invention, has approximate dimensions of 5×5×2 mm (2×2×1 in). As can be seen, its dimensions are relatively small and are very helpful for the design and construction of aspects of the invention proposed because it allows measuring static and dynamic acceleration in a similar manner than the natural vestibular system.

The accelerometers that may be used according to aspects of the present invention, include the one-axis or two-axis ADXL103/ADXL203™ accelerometers manufactured by Analog Devices, Inc., which are high precision sensors with low consumption and low power included in a monolithic integrated circuit that is capable of detecting dynamic acceleration (i.e. vibration) and static acceleration (gravitational pull).

Simulation of the Informative Process at the Semicircular Canals

The artificial sensors detecting angular displacements are the gyroscopes. The vestibular prosthesis of aspects of the present invention uses gyroscopes to reproduce the function carried out by the semicircular channels of the natural vestibule. The rotation can take place without observing any changes in the linear acceleration. For example, when the axes of the sensors X and Y are in a position parallel to the surface of the Earth and the Z-axis is pointing towards the centre of the Earth, the Z-axis delivers a measurement of 1°, while the X and Y-axes obtain a measurement of 0°.

When turning the movement sensor around the Z-axis only, the X and Y-axes never abandon the 0° measurement because they suffer no linear displacements in any direction, since the Z-axis continues to always deliver the 1° measurement because it always remains in the same place, without moving forward or backward. Therefore, we understand from this mode that in order to detect the body's rotation movement, the gyroscopes must be used.

It is common to find a multi-axis gyroscope and accelerometer, intended to measure fundamental movement, in one single inertial measurement unit (IMU). However, for the vestibular prosthesis of aspects of the present invention, we chose an ADXRS623™ gyroscope from Analog Devices, Inc. The gyroscope provides a voltage output proportional to the angular acceleration, and in order to create a three-dimensional detection system, three sensors are required, each one of which is placed in one of the sensitivity axes X, Y, Z to have sensors in the three spatial planes. Three ADXRS623™ gyroscopes, or its equivalent, ADXRS623™ which is a sensor system with only one sensitivity axis (Z, for example) must be used for this reason. In that case, it produces a positive voltage for clockwise rotations and a negative one for counter clockwise rotations. The sensor's output is used as the input for the Mathematical Model of the Vestibule with the purpose of obtaining a stimulation pattern that is a complex function of the acceleration detected by the sensor.

The information provided by the sensors, gyroscopes and accelerometers can be once again turned into a signal pattern, with which the vestibular pathways or the periauricular region can be stimulated through electrodes, enabling the brain to integrate this information to generate the appropriate postural reflexes. The system described in this manner would work as a vestibular prosthesis; that is to say, it could be an aid so the brain has the information to control the vertical posture on time.

Due to the fact that two gyroscopes with an inverted sensitivity axis regarding each other in each spatial plane are included, the scheme of FIG. 4 includes two processing lines, one for each of these gyroscopes, which are referred to as left and right therein.

Microgyroscopes and Semicircular Canals

As noted in the previous paragraph, the input for the semicircular canals model is the angular acceleration, which is obtained by deriving the signal obtained by the gyroscope. Even though a derivation amplifies the errors in the sensor's measurements, it is possible to obtain the angular acceleration directly with the measurement of the angular velocity if the model of the cupula-endolymphatic system is modified for each semicircular canal.

The mechanical coupling equations for two contralateral vertical semicircular canals, in matrix form:

$$\dot{X} = NX + +B\dot{\omega}.$$

where $y_1 = \dot{x}_1 : y_2 = \dot{x}_2 \cdot x_1$ is the displacement of the ciliary bundle in a vertical semicircular canal and $x_2$ is the displacement of the ciliary bundle in the contralateral vertical semicircular canal.

where: $y_1 = \dot{x}_1; \dot{x}_2 = y_2;$ $$X = \begin{pmatrix} x_1 \\ y_1 \\ x_2 \\ y_2 \end{pmatrix};$$

$$\omega = \begin{pmatrix} 0 \\ \omega_1 \\ 0 \\ \omega_2 \end{pmatrix};$$

$$N = \begin{pmatrix} 0 & 1 & 0 & 0 \\ -\frac{1}{\tau_2} & -\frac{1}{\tau_2 \tau_1} & 0 & -\lambda_{12} \\ 0 & 0 & 0 & 1 \\ 0 & -\lambda_{21} & -\frac{1}{\tau_2 \tau_1} & -\frac{1}{\tau_2} \end{pmatrix};$$

$$B = \begin{pmatrix} 0 \\ \frac{R_1}{k_1^2}\left(1 + \frac{l_1}{L_1}\right) \\ 0 \\ \frac{R_2}{k_2^2}\left(1 + \frac{l_2}{L_2}\right) \end{pmatrix}.$$

If $\det N \neq 0$, the system's general solution in an integral manner is given by:

$$X(t) = e^{N(t-t_0)} X(t_0) + \int_{t_0}^{t} e^{N(t-t_0)} B\dot{\omega}(\hat{t}) d\hat{t},$$

If $t_0 = 0$ and integrating by parts results in:

$$X(t) = e^{Nt}(X(0) - B\omega(0)) + B\omega(t) + N\int_{t_0}^{t} e^{N(t)} B\omega(\hat{t}) d\hat{t},$$

Then, the displacement of the cupula can be obtained directly based on the gyroscope's information, only needing the numeric solution of the integral appearing in the previous equation, which in practical situations is more appropriate than deriving.

Modes of Operation/Functioning of the Vestibular Prosthesis

We have mentioned two modes of operation for the prosthesis. 1) in the form of stimulation pulses applied directly to the vestibule by means of implanted electrodes. 2) in the form of direct current (galvanic), applied to the surface of the temporal periauricular region by means of non-implanted surface electrodes.

Mode 1. Invasive Implantation of Electrodes

This case will be possibly used in individuals with severe damage to the structures of the vestibular system, forcing the complete replacement of the natural organ, similarly to what is done in the case of cochlear implants that are broadly used all over the world today. The implantation and the electrode type to be used will be carried out in the manner already known in the state of the art.

Mode 2. Vestibular Galvanic Stimulation by Means of Non-Implanted electrodes

The vestibular galvanic stimulation (VGS) has been used to study the operation of the vestibular system because a response is obtained from this system naturally without exciting other sensory systems.

The VGS is a simple, safe and specific way to produce vestibular reflexes. A controlled current force delivering≈1 mA is used. The stimulation causes the person to lean towards one of the sides. The stimulation has different forms:

Bilateral Bipolar VGS

Two electrodes are placed in the subject's mastoid apophysis. The stimulation current goes in the direction of one of the electrodes, which is why one of them has a greater potential than the other. The electrode with the greatest potential, increases the vestibular afferent cells' discharge frequency, while, at the opposite side, the afferent cells, decrease their discharge frequency, which would translate into a sensation of unbalance towards the positive electrode.

Unilateral Bipolar VGS—

In this stimulation form, one of the electrodes is placed in the subject's forehead and another is placed in the subject's mastoid apophysis. The central nervous system (CNS) must use the discrepancy between the left vestibular activity and the right to orient the response in balance. As in the case of the bilateral bipolar VGS, a postural response is induced while one of the sides is excited in which the opposite side is inhibited, but, in this case, the vestibular response of the non-stimulated site takes place naturally. The inclination observed is towards the electrode with the greatest potential.

Unipolar Bilateral VGS—

The subjects lean forward with cathodic VGS and backward with anodic VGS.

The response comes from a change in the vestibular input, which probably modulates the afferent's tonic discharge, acting directly in the one that is close to the post-synaptic trigger site. The cathodic current increases the discharge frequency, while the anodic current decreases it. The response is due to the activations of the reticulospinal, vestibular spinal and rubrospinal tracts.

EXAMPLE

Vestibular Galvanic Stimulation (VGS)

Results

Figure 6:
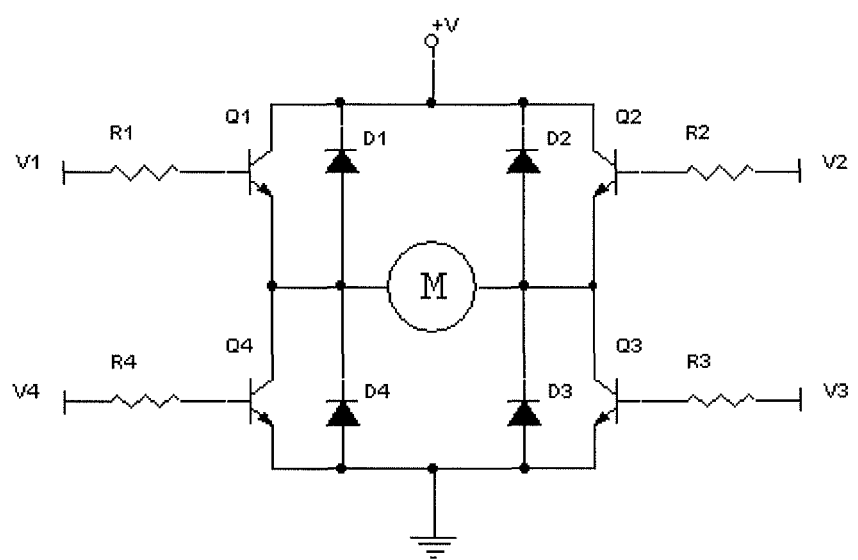
FIG. 6. Shows the electronic diagram of the bridge H, according to various aspects of the present invention.

The stimulator used is a current amplifier known as bridge H (see FIG. 6). When using a 9 V battery and a 0-50 K$\Omega$ precision potentiometer at the input, a current range at the output ranging between 0.2 to 1.3 mA is obtained. When using a 9 V battery and a 0-50 K$\Omega$ precision potentiometer, a current range at the output ranging between 0.2 to 1.3 mA is obtained. The electrodes consist of two 5-mm diameter silver chloride circular pieces adhered to the subject's mastoid region.

A VGS stimulation test was carried out in 13 healthy subjects, women and men, from 20 to 35 years old. From these, 7 received bilateral bipolar stimulation while they walked, 3 received monaural bipolar stimulation while they walked, 2 received bilateral bipolar stimulation while they remained standing and 1 monaural bipolar while he remained standing. The observations in both forms yield the following results A, B and C, shown in FIGS. 7A, 7B and 7C.

Figure 7A:
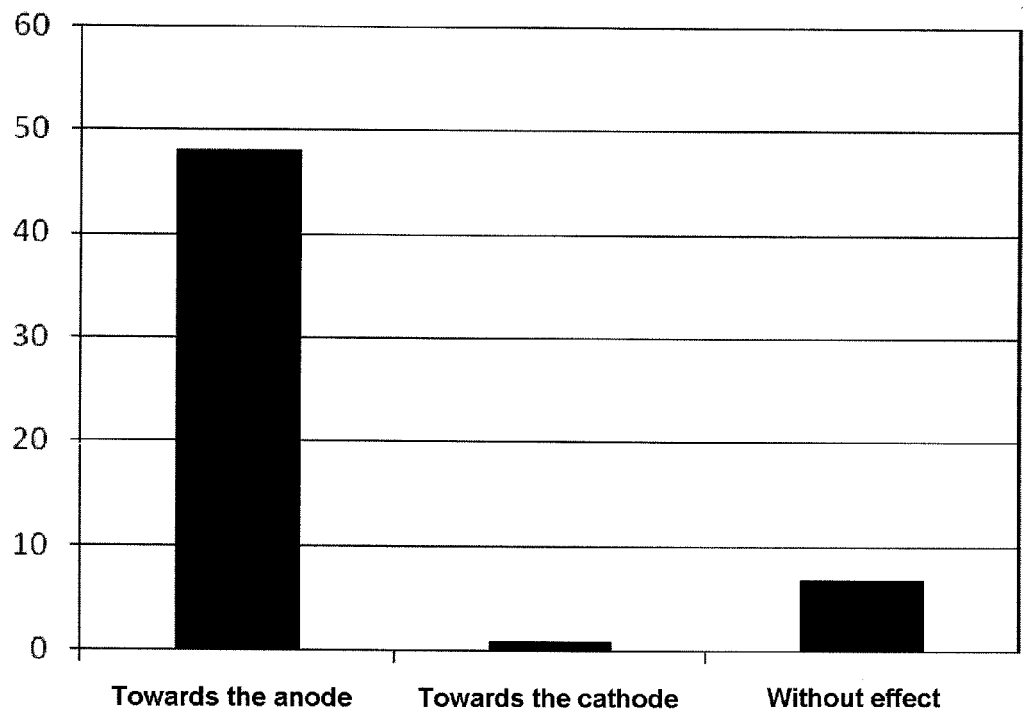
FIG. 7A. Shows the results of the galvanic electrical stimulation in normal subjects graphically, applying/using bilateral bipolar stimulation in individuals walking.

From which:

Result A. Is the result of the bilateral bipolar stimulation applied 16 times on 7 subjects while they walked. The subjects mainly deviated their paths towards the anode. The results are shown in FIG. 7A.

Figure 7B:
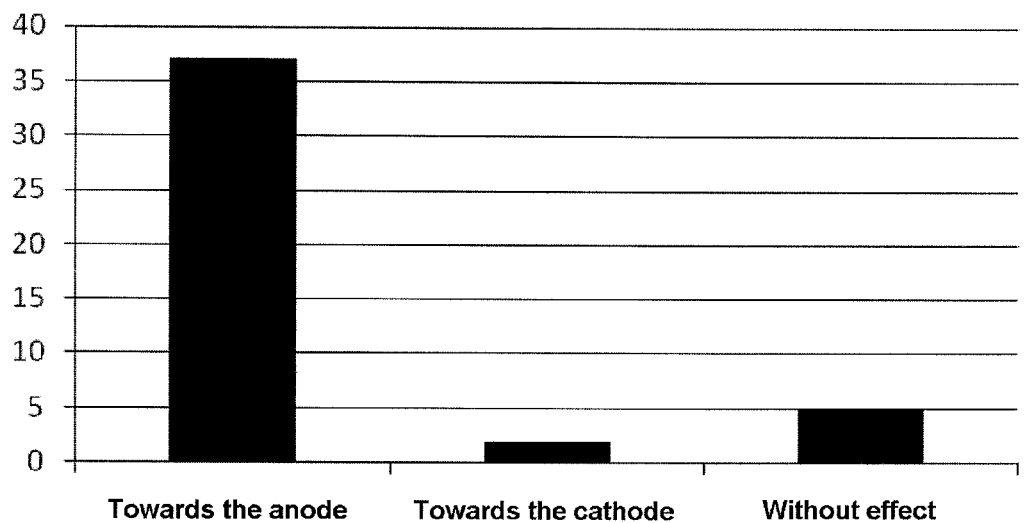
FIG. 7B. Shows the results of the galvanic electrical stimulation in normal subjects graphically, applying/using unilateral bipolar stimulation in individuals walking FIG. 7C. Shows the results of the galvanic electrical stimulation in normal subjects graphically, applying/using bilateral bipolar stimulation in individuals standing still.

Result B. Is the result of the unilateral bipolar stimulation applied 16 times on three subjects while they walked. The subjects mainly deviated their paths towards the anode. The results are shown in FIG. 7B.

Figure 7C:
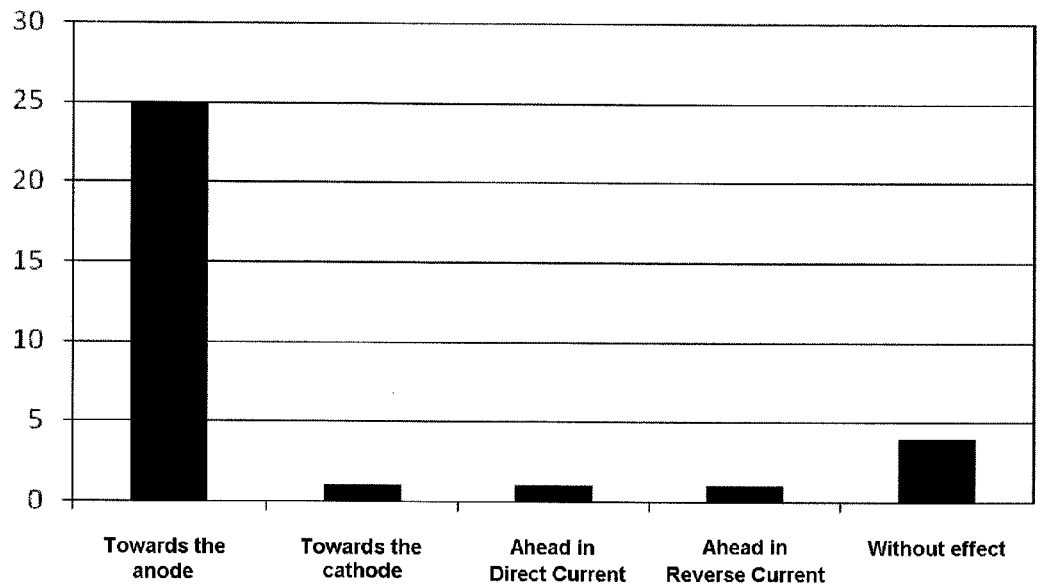
Figure 8:
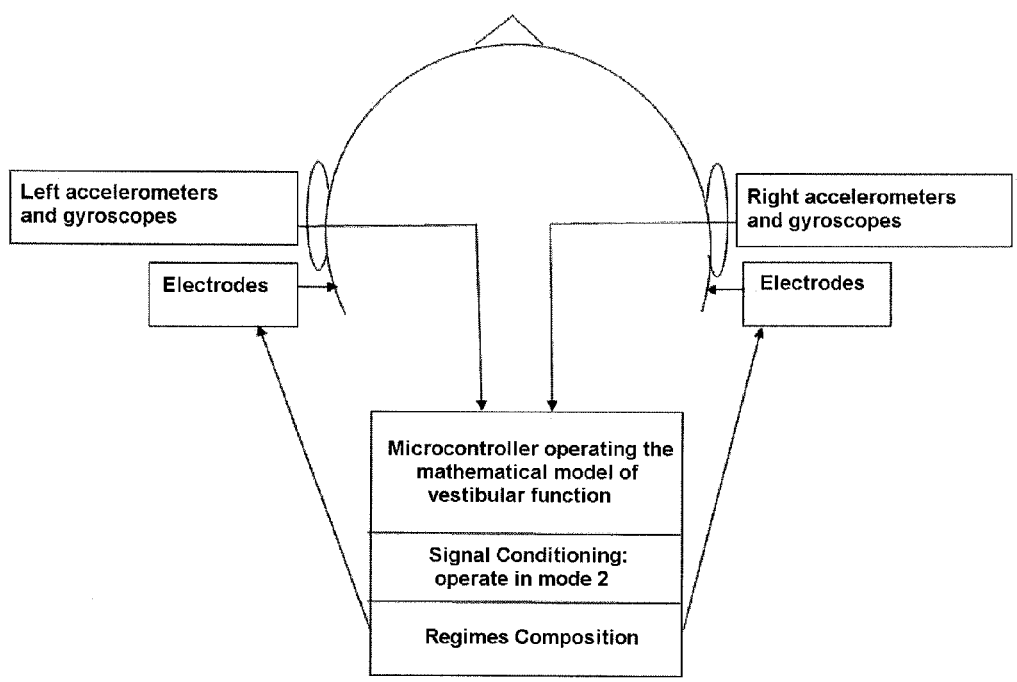
FIG. 8. Schematically illustrates the vestibular prosthesis according to various aspects of the present invention and the stimulation systems when used in mode 2.

Result C. Is the result of the bilateral bipolar stimulation applied 16 times on two subjects while they remained standing. The subjects mainly displaced the centre of body mass towards the anode. The results are shown in FIG. 7C.

The displacement in the X-axis and the Y-axis and the displacement angle between the two axes was compared in real time before, during and after the stimulation.

The study carried out until now indicates that the use of the surface galvanic stimulation is feasible for the development of aids (vestibular prosthesis) giving information to the subject about his or her orientation and about the displacement of his or her head, combining the detection system proposed with the findings related to this type of stimulation. This will allow having a high level form of non-implantable vestibular prosthesis, which facilitates its development and study enormously.

In one of the variations of the present invention, when operating in mode 2, consists in installing the device we have developed in healthy subjects and studying the capacity of the system to provide them with information about their orientation and the head's accelerated movement.

Since the subjects experience a sensation of movement when the stimulus is applied with their eyes opened or closed, we can conclude that the vestibular galvanic stimulation directly influences the vestibular system, as proven by other studies. These other studies propose that a hyperpolarization in one of the vestibular organs and the depolarization on the opposite side are imposed through the applied current. As previously explored, the inclination towards one of the sides of the head in a monkey depolarizes the ipsilateral hair cells, causing an increase in the discharge frequency of the primary vestibular afferent cells; simultaneously, the hair cells of the opposite side are hyperpolarized, which translates into a decrease in the trigger frequency of the primary afferent cells. The effect produced by the bilateral bipolar galvanic stimulation is similar, yet not completely identical, to the head's natural inclination towards the greatest potency.

It should be noted that it presents practically the same effect in the monaural bipolar stimulation, therefore, when using a vestibular prosthesis, it is very likely that stimulating the sides would be enough for the opposite vestibule to react on its own, making the prosthesis less invasive.

Electrode System for a Galvanic Surface Stimulation

Figure 9:
FIG. 9. Shows the diadem with a group of electrodes that allow the complex stimulation in the periauricular area, according to various aspects of the present invention.

For this type of stimuli, the electrode system developed consists of a diadem placed on the head (see FIG. 9) in the same manner than an old headphone system. The end part of this diadem completely surrounds the ear's pinna. The diadem has a set of non-polarizable silver chloride electrodes adhered to this part (white circles). 5-mm diameter electrodes are used in aspects of the present invention, but there can be multiple variables of these electrodes.

The shape, number, size and all other characteristics of the electrodes are to variable and have the purpose of stimulating diverse areas of the periauricular region in a selective manner, reaching all the structures of the vestibule and inducing complex movement sensations in this manner, thus being able to stabilize the subject's position with the purpose of activating the vestibular system indirectly.

The electrode system is connected to the output of the conditioning system, which is, in turn, controlled by the microprocessor receiving the input from the MEMS and it process the information using the mathematical model of the vestibular function, thus generating a specific electrical stimulation pattern that is a function of the movement of the subject's head.

Figure 10:
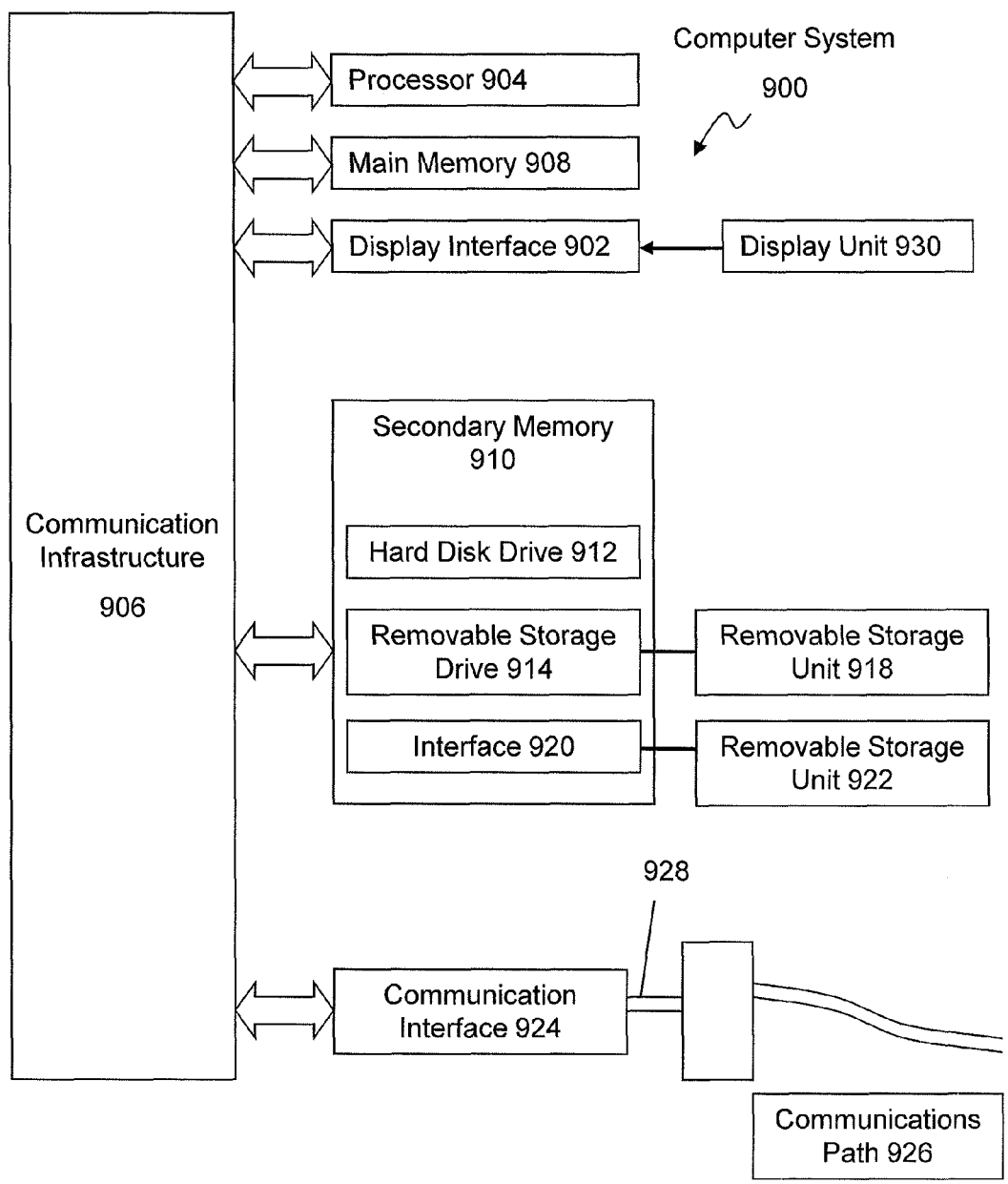
FIG. 10 presents an example system diagram of various hardware components and other features, for use in accordance with an aspect of the present invention.

According to various aspects, the electrode system may be monitored via a combination of hardware and software combination. For example, FIG. 10 presents an example system diagram of various hardware components and other features, for use in accordance with an aspect of the present invention. The present invention may be implemented using hardware, software, or a combination thereof and may be implemented in one or more computer systems or other processing systems. In one aspect, the invention is directed toward one or more computer systems capable of carrying out the functionality described herein. An example of such a computer system 900 is shown in FIG. 10.

Computer system 900 includes one or more processors, such as processor 904. The processor 904 is connected to a communication infrastructure 906 (e.g., a communications bus, cross-over bar, or network). Various software aspects are described in terms of this example computer system. After reading this description, it will become apparent to a person skilled in the relevant art(s) how to implement the invention using other computer systems and/or architectures.

Computer system 900 can include a display interface 902 that forwards graphics, text, and other data from the communication infrastructure 906 (or from a frame buffer not shown) for display on a display unit 930. Computer system 900 also includes a main memory 908, preferably random access memory (RAM), and may also include a secondary memory 910. The secondary memory 910 may include, for example, a hard disk drive 912 and/or a removable storage drive 914, representing a floppy disk drive, a magnetic tape drive, an optical disk drive, etc. The removable storage drive 914 reads from and/or writes to a removable storage unit 918 in a well-known manner. Removable storage unit 918, represents a floppy disk, magnetic tape, optical disk, etc., which is read by and written to removable storage drive 914. As will be appreciated, the removable storage unit 918 includes a computer usable storage medium having stored therein computer software and/or data.

In alternative aspects, secondary memory 910 may include other similar devices for allowing computer programs or other instructions to be loaded into computer system 900. Such devices may include, for example, a removable storage unit 922 and an interface 920. Examples of such may include a program cartridge and cartridge interface (such as that found in video game devices), a removable memory chip (such as an erasable programmable read only memory (EPROM), or programmable read only memory (PROM)) and associated socket, and other removable storage units 922 and interfaces 920, which allow software and data to be transferred from the removable storage unit 922 to computer system 900.

Computer system 900 may also include a communications interface 924. Communications interface 924 allows software and data to be transferred between computer system 900 and external devices. Examples of communications interface 924 may include a modem, a network interface (such as an Ethernet card), a communications port, a Personal Computer Memory Card International Association (PCMCIA) slot and card, etc. Software and data transferred via communications interface 924 are in the form of signals 928, which may be electronic, electromagnetic, optical or other signals capable of being received by communications interface 924. These signals 928 are provided to communications interface 924 via a communications path (e.g., channel) 926. This path 926 carries signals 928 and may be implemented using wire or cable, fiber optics, a telephone line, a cellular link, a radio frequency (RF) link and/or other communications channels. In this document, the terms "computer program medium" and "computer usable medium" are used to refer generally to media such as a removable storage drive 980, a hard disk installed in hard disk drive 970, and signals 928. These computer program products provide software to the computer system 900. The invention is directed to such computer program products.

Computer programs (also referred to as computer control logic) are stored in main memory 908 and/or secondary memory 910. Computer programs may also be received via communications interface 924. Such computer programs, when executed, enable the computer system 900 to perform the features of the present invention, as discussed herein. In particular, the computer programs, when executed, enable the processor 910 to perform the features of the present invention. Accordingly, such computer programs represent controllers of the computer system 900.

In an aspect where the invention is implemented using software, the software may be stored in a computer program product and loaded into computer system 900 using removable storage drive 914, hard drive 912, or communications interface 920. The control logic (software), when executed by the processor 904, causes the processor 904 to perform the functions of the invention as described herein. In another aspect, the invention is implemented primarily in hardware using, for example, hardware components, such as application specific integrated circuits (ASICs). Implementation of the hardware state machine so as to perform the functions described herein will be apparent to persons skilled in the relevant art(s).

In yet another aspect, the invention is implemented using a combination of both hardware and software.

Figure 11:
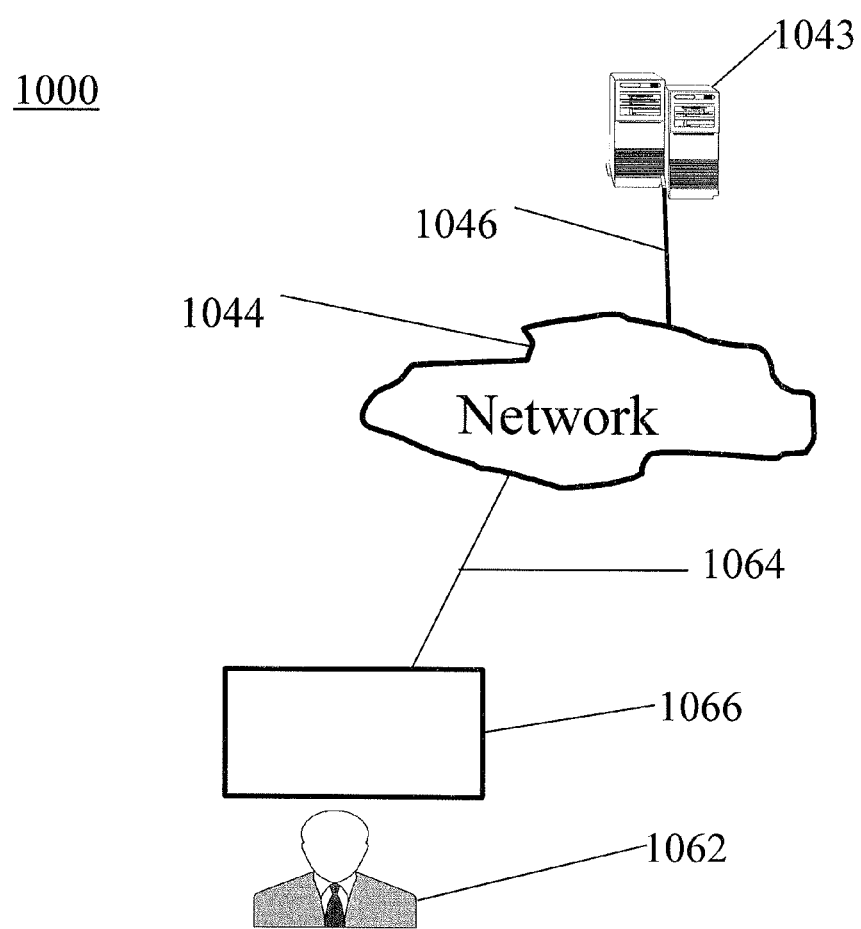
FIG. 11 is a block diagram of various example system components, in accordance with an aspect of the present invention.

FIG. 11 is a block diagram of various example system components, in accordance with an aspect of the present invention. FIG. 11 shows a communication system 1000 usable in accordance with the present invention. The communication system 1000 may include one or more accessors 1062 (also referred to interchangeably herein as one or more "users") and a terminal 1066. According to various aspects, the terminal 1066 may include a processor and one or more electrode system such as the electrode system described above. In one aspect, data for use in accordance with the present invention is, for example, input and/or accessed by accessors 1062 via terminal 1066, such as a personal computer (PC), minicomputer, mainframe computer, microcomputer, telephonic device, or wireless devices, such as a personal digital assistant ("PDA") or a hand-held wireless device, such device optionally further including, for example, one or more sensing devices and/or connections to such devices (e.g., an electrode system), coupled to a server 1043, such as a PC, minicomputer, mainframe computer, microcomputer, or other device having a processor and a repository for data and/or connection to a repository for data, via, for example, a network 1044, such as the Internet or an intranet, and couplings 1046 and 1064. The couplings 1046 and 1064 include, for example, wired, wireless, or fiberoptic links.

Even though aspects of the invention have been described by referring to various aspects of the present invention and examples regarding a micro-electro-mechanical system simulating the vestibular function, the invention's scope and spirit includes the incorporation or its use with any system and/or appropriate mechanical device. Therefore, it must be understood that numerous and varied modifications can be carried out without departing from the spirit of the invention.

The invention claimed is:

1. A vestibular prosthesis for a patient, comprising:
one or more micro-electric-mechanical (MEMS) sensors, including at least one pair of gyroscopes in each of three orthogonal axes and at least one pair of accelerometers in each of the three orthogonal axes, to detect an angular and linear movement providing displacement measurements;
at least one microprocessor coupled to the MEMS sensors, wherein the microprocessor uses a mathematical model of an informative process of a vestibular mechanoreceptor to produce an output comprising one of an electric pulse pattern and a continuous galvanic current pattern;
a conditioning unit that amplifies and conditions the microprocessor output to apply current that is proportional to said output, to stimulation electrodes;
wherein the microprocessor is configured to:
determine a displacement of a cupula and an otolithic mass of the patient;
determine a membrane potential $V_1$ of one or more hair cells of the patient as a result of the displacement detected by the MEMS sensors by means of determining a transduction current $I_T$; and determine an action potential discharge pattern $V_2$ for a primary afferent neuron that synapses with the hair cell by means of the mathematical model of the informative process of the vestibular mechanoreceptor.

2. The vestibular prosthesis according to claim 1, characterized in that it has two modes of operation: a) mode 1, where a set of electrodes to provide electrical stimulation directly to the vestibular nerves (with the surgical implantation of the electrodes), connected to the output of the conditioning unit which receives the output of the microprocessor, provide electric pulses to the vestibular nerves; and b) mode 2, where a set of surface electrodes to provide electrical stimulation in the temporal region of the head (by contact without implantation), connected to the output of the conditioning unit which receives the output of the microprocessor, provide stimulation by means of the galvanic current in the periauricular region.

3. The vestibular prosthesis according to claim 1, characterized in that the processing of the mathematical model of the vestibular function allows determining the stimulation pattern based on the head's linear and angular acceleration by means of the microprocessor.

4. The vestibular prosthesis according to claim 1, characterized in that the a set of periauricular electrodes supported in a diadem-shaped system, which also support the MEMS sensors, that allows to transmit electrical stimulation to the patient.

5. The vestibular prosthesis according to claim 1, characterized in that the diadem-shaped set of electrodes allows stimulating the periauricular temporal region with diverse galvanic current patters applied on said electrodes, and where the number of electrodes is at least eight each side.

6. The vestibular prosthesis according to claim 1, characterized in that it has two modes of operation: a) mode 1, where a set of surgically implanted electrodes provide electrical stimulation directly to the vestibular nerves using electrical pulses, and that are connected to the output of the conditioning unit which receives the output of the microprocessor; and b) mode 2, where a set of surface electrodes provide electrical stimulation in the temporal periauricular region of the head by contact and without implantation using galvanic current, and that are connected to the output of the conditioning unit which receives the output of the microprocessor.

* * * * *

UNITED STATES PATENT AND TRADEMARK OFFICE
CERTIFICATE OF CORRECTION

PATENT NO. : 8,855,774 B2
APPLICATION NO. : 13/619105
DATED : October 7, 2014
INVENTOR(S) : Enrique Soto-Eguibar et al.

It is certified that error appears in the above-identified patent and that said Letters Patent is hereby corrected as shown below:

On the Title Page

Item (75) Inventors:    Enrique Soto-Eguibar, Puebla (MX); Maria Del Rosario Guadalupe Vega-Y Saenz De Miera, Puebla (MX); Tamara Alexandrova, Puebla (MX); Vladimir Aleksandrov, Puebla (MX); Adriana Cristina Pliego Carrillo, Puebla (MX); Wuiyevaldo Fermin Guerrero Sanchez, Puebla (MX)

should read as

Item (75) Inventors:    Enrique Soto-Eguibar, Puebla (MX); Maria Del Rosario Guadalupe Vega-Y Saenz De Miera, Puebla (MX); Tamara Alexandrova, Puebla (MX); Vladimir Aleksandrov, Puebla (MX); Maribel Reyes-Romero, Puebla (MX); Adriana Cristina Pliego Carrillo, Puebla (MX); Wuiyevaldo Fermin Guerrero Sanchez, Puebla (MX)

Signed and Sealed this
Sixth Day of January, 2015

Michelle K. Lee
*Deputy Director of the United States Patent and Trademark Office*